(12) United States Patent
Ditrich et al.

(10) Patent No.: US 6,720,447 B1
(45) Date of Patent: Apr. 13, 2004

(54) METHOD FOR THE PRODUCTION OF ESTERS

(75) Inventors: Klaus Ditrich, Gönnheim (DE); Ulrich Block, Friedelsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/889,401

(22) PCT Filed: Jan. 29, 2000

(86) PCT No.: PCT/EP00/00702
§ 371 (c)(1),
(2), (4) Date: Jul. 17, 2001

(87) PCT Pub. No.: WO00/46177
PCT Pub. Date: Aug. 10, 2000

(30) Foreign Application Priority Data

Feb. 3, 1999 (DE) .......................... 199 04 207

(51) Int. Cl.[7] .......................... C07C 69/66; C07C 69/63
(52) U.S. Cl. .................. 560/179; 560/226; 560/227
(58) Field of Search ................... 560/179, 226, 560/227

(56) References Cited

U.S. PATENT DOCUMENTS

| | | | |
|---|---|---|---|
| 4,082,788 A | * | 4/1978 | Mims |
| 5,057,607 A | | 10/1991 | Zmijewski |
| 5,202,463 A | | 4/1993 | Ruszkay |
| 5,637,761 A | * | 6/1997 | Miltenberger et al. |
| 5,648,529 A | * | 7/1997 | Jones et al. |

FOREIGN PATENT DOCUMENTS

EP        361 839        4/1990

OTHER PUBLICATIONS

Derwent Abst–XP–002139633.
Derwebt Abst–XP–002139634.
J. of Chem.Soc., Iss 0022–4936—957–958, No. 14, Jul. 14,1988 Gotor et al.
J ofAmChem.Soc., 111, 1989 3904–3095, Kitaguchi et al.

* cited by examiner

Primary Examiner—Johann Richter
Assistant Examiner—Paul A. Zucker
(74) Attorney, Agent, or Firm—Keil & Weinkauf

(57) ABSTRACT

The present invention relates to a novel process for the preparation of esters of the general formula I

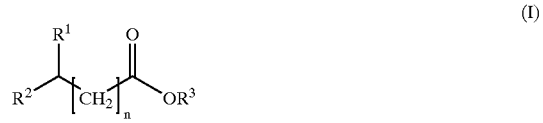

(I)

from compounds of the general formula II contained in aqueous solutions

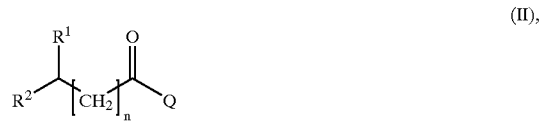

(II), which comprises a) extracting the compounds of the general formula II directly or after liberation from their salts in the presence of a $C_1$–$C_8$-alcohol and a water-immiscible solvent and b) then esterifying with the $C_1$–$C_8$-alcohol in the presence of a catalyst and of an entraining agent under the conditions of an azeotropic distillation, where the process steps (a) and (b) can be carried out separately in terms of time and space or else in a successive continuous or batchwise sequence and where the variables and substituents in the formulae I and II have the following meanings:

$R^1$=F, Cl, —OH, —O$C_1$–$C_{10}$-alkyl,
$R^2$=H, $C_1$–$C_{10}$-alkyl;
$R^3$=$C_1$–$C_8$-alkyl,
Q=—OH, —O$^-$K$^+$, where K$^+$ is an alkali metal cation or alkaline earth metal cation,
n=0, 1 or 2.

18 Claims, 2 Drawing Sheets

METHOD FOR THE PRODUCTION OF ESTERS

This application is a 371 of PCT/EP00/00702 filed Jan. 29, 2000.

The present invention relates to a novel process for the preparation of esters of the general formula I and a process for the extraction of compounds of the formula II.

Esters of the general formula I are valuable intermediates for the resolution of amines by enzyme-catalyzed reaction with these esters.

Thus Kitaguchi et al. (J. Amer. Chem. Soc. 111, 3094–3095, 1989) describe, for example, the resolution of amines using trifluoroethyl butyrate under subtilisin catalysis. The enantioselective acylation of 2-aminobutan-1-ol using ethyl acetate under catalysis by porcine pancreas lipase (PPL) is described by Gotor et al. (J. Chem. Soc. Chem. Commun. 957–958, 1988).

Quiros et al. (Tetrahedron: Asymmetry 4, 1105–1112, 1993) describe the lipase-catalyzed synthesis of optically active amides from racemic α-halo-substituted ethyl propionates and primary amines.

In U.S. Pat. No. 5,057,607, a process for the stereoselective acylation of primary amines with esters which carry an oxygen atom in the vicinity of the carbonyl carbon is described for the synthesis of β-lactams.

WO 95/08636 describes a process for the resolution of primary and secondary amines in the presence of an ester using a hydrolase.

In the enzyme-catalyzed kinetic resolution of amines described in WO 95/08636 one enantiomer is converted into the amide. For this enzymatic acylation reaction, esters are preferably used which carry an oxygen atom in the α-position to the carbonyl carbon, such as, for example, methoxyacetic acid esters. The free amine is obtained from the amide formed in this reaction by cleavage with a base. In this process, in addition to the amine, the acid, for example methoxyacetic acid, is obtained in aqueous solution in the form of its salts. It is important for the economy of the process to make this acid available again for the acylation reaction, that is to convert it into its ester again, which can then be used afresh in the enzymatic acylation.

Customarily, esters of this type are formed from the acids in the presence of an alcohol and of a mineral acid as a catalyst. This ester formation takes place, however, only up to an equilibrium.

In cases in which the boiling points of the acids, alcohols and esters are above that of water, the equilibrium can be easily shifted by removing the water by means of a distillation. If the boiling points are under that of water, this method cannot be used.

In the literature, a number of methods are described in which it was attempted to gain control of the problem of the lower boiling points of the esters and alcohols. In DE 195 39 293, for example, a process for the preparation of alkyl cyanoacetates is thus described in which the water is removed by means of an azeotropic distillation. The disadvantage of this process is that a complete conversion cannot be achieved under the conditions described.

CH 527 156 likewise describes a process for the preparation of esters of high-boiling carboxylic acids. In this process, the equilibrium and thus the reaction is affected by a large excess of alcohol. It is disadvantageous that the alcohol removed by means of the distillation must be continually supplemented during the reaction.

A disadvantage in the azeotropic distillations described above is that the water of reaction cannot be completely removed and that as a result a complete conversion is not possible.

In EP-B-0 361 839, a process is described which does not have this disadvantage. EP-B-0 361 839 claims a process for the dehydration of substances and mixtures, carried out by continuous azeotropic distillation using an organic solvent which forms a virtually immiscible azeotropic mixture of minimum boiling point with water, the condensation distillate being cooled to at least a temperature at which the condensate is supersaturated with a given water content or the organic phase of the condensate is supersaturated with water, as a result of which a further separation of water is facilitated. Unfortunately, this process is not widely applicable and necessitates cooling of the condensate as a further process step.

In U.S. Pat. No. 5,202,463, a multi-stage process for the removal of the water which is formed in the esterification is described. This process therefore necessitates a high outlay in terms of apparatus.

Since none of the known processes makes possible a reaction to give the esters which is as complete as possible and can be carried out readily and simply, the object is therefore to develop an appropriate process which does not have the disadvantages of the abovementioned processes and makes possible a simple, inexpensive preparation of esters from the acids contained in aqueous solution.

We have found that this object is achieved by a process for the preparation of esters of the general formula I from compounds of the general formula II contained in aqueous solutions which comprises
a) extracting the compounds of the general formula II directly or after liberation from their salts in the presence of a $C_1$–$C_8$-alcohol and a water-immiscible solvent and
b) then esterifying with the $C_1$–$C_8$-alcohol in the presence of a catalyst and of an entraining agent under the conditions of an azeotropic distillation, where the process steps (a) and (b) can be carried out separately in terms of time and space or else in a successive continuous or batchwise sequence and where the variables and substituents in the formulae I and II have the following meanings:

$R^1$=F, Cl, —OH, —$OC_1$–$C_{10}$-alkyl,
$R^2$=H, $C_1$–$C_{10}$-alkyl
$R^3$=$C_1$–$C_8$-alkyl,
Q=—OH, —$O^-K^+$, where $K^+$ is an alkali metal cation or alkaline earth metal cation or an amine,
n=0, 1 or 2, preferably 0 or 1, particularly preferably 0.

In the compounds of the formulae (I) and (II), $R^1$ is fluorine, chlorine, hydroxyl or substituted or unsubstituted, branched or unbranched —$OC_1$–$C_{10}$-alkyl.

—O-alkyl radicals which may be mentioned are substituted or unsubstituted, branched or unbranched —O—$C_1$–$C_{10}$-alkyl chains in which the bonding of the chains to the parent structure of the formulae takes place via an oxygen atom and in which the alkyl radicals have, for example, the following meaning: methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Preferred radicals which may be mentioned are methyl, ethyl or n-propyl.

$R^2$ in the compounds of the formulae I and II is hydrogen or substituted or unsubstituted, branched or unbranched $C_1$–$C_{10}$-alkyl.

Alkyl radicals which may be mentioned are substituted or unsubstituted, branched or unbranched $C_1$–$C_{10}$-alkyl chains such as, for example, methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Preferred radicals which may be mentioned are hydrogen, methyl, ethyl or n-propyl. Hydrogen or the methyl radical is particularly preferred.

$R^3$ in the compounds of the formula I is substituted or unsubstituted, branched or unbranched $C_1$–$C_8$-alkyl.

Alkyl radicals which may be mentioned are substituted or unsubstituted, branched or unbranched $C_1$–$C_{10}$-alkyl chains such as, for example, methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Preferred radicals which may be mentioned are ethyl, n-propyl, isopropyl, butyl, hexyl or octyl. The isopropyl radical is particularly preferred.

Possible substituents of the radicals $R^1$, $R^2$ and $R^3$ mentioned are substituents such as F, Cl, Br, CN, O—$CH_3$ and/or O-phenyl.

The variable Q in the compounds of the general formula I is hydroxyl or —$O^-K^+$, where $K^+$ is an alkali metal or alkaline earth metal cation or an amine. Alkali metal or alkaline earth metal cations which may be mentioned by way of example are the cations of lithium, sodium, potassium or calcium. Those of sodium or potassium are preferred. Amine is understood as meaning, for example, organic amines or $NH_3$.

In the process according to the invention, the acids to be used for the esterification are first liberated from their salts, if necessary, in the aqueous solution. For this, suitable acids are all those whose $pK_a$ is lower than the $pK_a$ Of the compounds of the general formula II (Q=OH). In the case of methoxyacetic acid, these are all acids which have a $pK_a$ smaller that about 2 and can thus liberate methoxyacetic acid from its salt, for example its sodium salt. Suitable acids are, for example, mineral acids such as sulfuric acid, hydrochloric acid, nitric acid, phosphoric acid or organic acids such as formic acid, oxalic acid, chloroacetic acid, fluoroacetic acid, cyanoacetic acid, benzenesulfonic acid, o- or p-toluenesulfonic acid, methanesulfonic acid, trifluoromethanesulfonic acid or trifluoroacetic acid. The use of sulfuric acid or p-toluenesulfonic acid is preferred, the use of sulfuric acid, in particular, being preferred for reasons of cost.

The acid can also be liberated by means of an acidic ion exchanger which has a $pK_a$ which is able to free the acid from its salt.

After liberation of the acids of the general formula II (Q=OH) from their salts, these are extracted with a $C_1$–$C_8$-alcohol and an apolar organic water-immiscible solvent. Solvents of this type are to be found in a number of substance classes, for example under the straight-chain or branched-chain saturated or unsaturated hydrocarbons such as n-heptane, n-heptene, n-octane or n-octene and their branched isomers, the saturated cyclic hydrocarbons such as cyclohexane or cycloheptane, open-chain or cyclic, saturated or unsaturated ethers or thioethers or aromatic compounds such as benzene, toluene or xylene. Aromatic compounds are preferred; toluene is particularly preferred.

Advantageously, the aqueous solution of the liberated acid is diluted with approximately 5% of water in order to prevent salts of the acid used for liberation, for example sulfuric acid, from precipitating.

The amount of the solvent mixture for the extraction is not critical. The solvent can be used for the extraction in a large excess. Advantageously, based on the aqueous solution of the acid, it is used in almost identical volumetric amounts, that is in a ratio of 1:1 or 1:1.5 based on the aqueous solution of the acid.

It is of crucial importance for the extraction yield in the process according to the invention that the extraction is carried out in the presence of a $C_1$–$C_8$-alcohol. Without the alcohol, the extraction yield is only a few percent. Suitable alcohols are methanol, ethanol, propanol, isopropanol, butanol and its isomers, and also pentanol, hexanol, heptanol and octanol and their branched isomers. Ethanol, propanol, isopropanol, butanol, hexanol or octanol is preferred. Isopropanol is particularly preferred. In principle, ketones are also suitable for improving the extraction. By means of the addition of alcohol, the acids can be extracted with a yield of at least 85%, preferably of at least 90%, particularly preferably of at least 95%.

During the extraction, a ratio of alcohol to organic solvent of 1:2 to 5:1 is advantageously established. Preferably, a ratio of alcohol to organic solvent of 1:1 to 3:1 is established. Particularly preferably, a 3:1 mixture is used. A further cosolvent such as cyclohexane is disadvantageous, as three phases are formed.

The alcohols can also be used simultaneously as solvents in the process according to the invention.

To improve the extraction results, salts can optionally be added.

In the process according to the invention, process step (a) [=extraction] can in principle be carried out at any temperature at which the alcohol and/or the solvent is not noticeably volatile and the extraction can be carried out as rapidly as possible. Advantageously, the extraction is carried out at a temperature of from 0° C. to 70° C. Preferably, the extraction is carried out at a temperature of from 20° C. to 50° C.

For the extraction, either the liberated acid or the alcohol can be initially introduced and/or the solvent and the other components in each case added. Advantageously, all components are mixed together at the same time. The extraction can be carried out batchwise, semicontinuously (repeated addition of one or more components) or continuously. The extraction is advantageously carried out continuously.

The acids preferably suitable for the process according to the invention lead to esters which carry an oxygen atom or fluorine atom in the vicinity of the carbonyl carbon in the acid component of the ester.

The vicinity of the carbonyl carbon is understood as meaning the bonding of the heteroatom to a carbon atom in the alpha-, beta-or gamma-position relative to the carbonyl carbon. Those acid components of the ester are preferred in which the heteroatom is bonded to the C-alpha atom. A preferred heteroatom is oxygen.

In the case of oxygen, the heteroatom can optionally be linked to further groups, e.g. alkyl groups. This leads to ethers.

Among these, the $C_{1-8}$-alkyl esters of $C_{1-4}$-alkoxyacetic acids, such as ethyl methoxyacetate, are preferred.

Suitable catalysts for the formation of esters from the extracted acids and the $C_1$–$C_8$-alcohols which were advantageously used in the extraction are, in principle, all catalysts which can catalyze ester formation, such as carbonates, acids or acidic ion exchangers. Acids which are advantageously suitable are strong to medium-strength inorganic or organic acids, such as sulfuric acid, hydrochloric acid, phosphoric acid, oxalic acid, formic acid, benzenesulfonic acid, toluenesulfonic acid, methanesulfonic acid, trifluoroacetic acid, fluoroacetic acid, mono-, di- or trichloroacetic acid or trifluoromethanesulfonic acid. For reasons of cost, sulfuric acid and p-toluenesulfonic acid are preferred, sulfuric acid being particularly preferred. Suitable ion exchangers are, for example, the various Amberlysts such as Amberlyst W38.

In the esterification, advantageously the same alcohols which were also already used for the extraction are used. However, other alcohols or alcohol mixtures can also be used.

For the process according to the invention, suitable entraining agents in process step (b) [esterification] are in principle all organic solvents which are immiscible with water and whose boiling point as an azeotrope with the alcohol and the water is lower by at least 8° C., preferably by at least 10° C., particularly preferably by at least 14° C. than that of the azeotrope of the alcohol and the water. Solvents which are advantageously suitable are, for example cyclohexane, cyclopentane, n-hexane, n-heptane, methylcyclohexane.

Preferably, cyclohexane is used as an entraining agent.

For the esterification, at least 1% by weight of entraining agent is used based on the total volume of the reaction. It can also be used in a large excess. Advantageously, 5 to 50% by weight of entraining agent, particularly preferably 5 to 20% by weight, very particularly preferably 5 to 10% by weight of entraining agent is used for the esterification.

The esterification is advantageously carried out at a temperature of from 50° C. to 100° C., particularly preferably of from 60° C. to 90° C.

The process according to the invention can be carried out at normal pressure or at elevated or reduced pressure. At the same time, the process steps (a) and (b) can be carried out at identical or different pressures. Preferably, the process is carried out at normal pressure or elevated pressure.

The water content in the esterification reaction can be lowered below 1%, preferably below 0.5%, particularly preferably below 0.1%, by means of the advantageous entraining agents. The water content was determined by Karl-Fischer titration. The low water content makes possible a yield of ester of at least 90%, preferably of at least 95%, particularly preferably of at least 97%, very particularly preferably of at least 99%.

Moreover, the reaction time in the esterification is markedly reduced by the use of the entraining agents. It can be more than halved by the use of the entraining agents, it being possible at the same time to achieve a quantitative conversion of the acids to the ester, whereas without entraining agent the reaction only proceeds up to a conversion of approximately 85% yield.

The course of the reaction in the process according to the invention can be readily monitored using customary methods, for example by means of HPLC, thin-layer chromatography or gas chromatography.

The invention is also suitable for the extraction of compounds of the formula II according to claim 1 from aqueous solutions, which comprises extracting the compounds of the general formula II directly or after liberation from their salts in the presence of a $C_1$–$C_8$-alcohol and a water-immiscible solvent.

The following examples serve to illustrate the invention.

In the enzyme-catalyzed kinetic resolution of amines, as is described in WO 95/08636, one enantiomer is converted into a methoxyacetamide (amide), whose cleavage with sodium hydroxide solution also yields sodium methoxyacetate (=NAMA) in addition to the desired free amine (see scheme I). The methoxyacetic acid (=MEA) bonded therein was liberated from its NAMA salt in the process according to the invention, and the MEA then dissolved in water was subsequently isolated by extraction and finally esterified to give the isopropyl ester (=MEIPE), which is then used again as an acylating reagent in the enzyme-catalyzed resolution.

Scheme I

Hydrolysis of the amide as exemplified by phenylethylamine

The central points of the process according to the invention are the use of isopropanol as a cosolvent in the extraction of the MEA from water, and the addition of cyclohexane as a coentraining agent in the azeotropic esterification of the extract.

EXAMPLE 1a

Liberation of the Acid From the Salt

The acid was liberated from 320 g of an aqueous solution of sodium methoxyacetate (NAMA), which was obtained from an amide cleavage using NaOH (see scheme II). The amide was obtained from a resolution, which had been carried out according to the process described in WO 95/08636.

Scheme II

Liberation of methoxyacetic acid

[structure: NAMA - sodium methoxyacetate] $\xrightarrow[\text{in water}]{H_2SO_4}$ [structure: MEA - methoxyacetic acid] + $Na_2SO_4$ in water Composition:

about 3% sodium hydroxide solution 37% sodium methoxyacetate (NAMA)

Procedure:

The aqueous solution was initially introduced at room temperature (about 23° C.), and treated with the sulfuric acid indicated above. In the course of this, the temperature rose to 65° C. and sodium sulfate precipitated. The mixture was cooled to room temperature with stirring and diluted with 175 ml of water; the solution thus obtained had a pH of 1.

The amount of water added was sufficient in order to keep the resulting sodium sulfate in solution at room temperature (>22° C.).

According to $^1$H-NMR and elemental analysis, the resulting solution had an MEA content of about 15% and an $Na_2SO_4$ content of 17%.

The solution obtained according to this procedure was employed, if not described otherwise, in the following extraction experiments.

EXAMPLE 1b

Extraction of the Acid From Aqueous Solution

Since MEA is unlimitedly miscible with water, it was not possible, as the experiments showed, to isolate it from the water satisfactorily using nonpolar solvents such as toluene, cyclohexane or ethers. On account of the low partition coefficients in these mixtures, the extraction yield was <5%.

By addition of an alcohol such as isopropanol, it was possible to carry out the extraction after liberation of the acid from its salt.

a) Extraction With Various Extracting Agent Mixtures:

Scheme III

Extraction of MEA

[structure: MEA in water] $\xrightarrow{\text{Extraction with toluene isopropanol}}$ [structure: MEA in toluene isopropanol]

Substances Employed:

40 g each of an aqueous solution of methoxyacetic acid (MEA) having the following composition:

18.5% of methoxyacetic acid (MEA) about 18% of sodium sulfate 40 g each of extracting agent mixture having the composition described in Table I.

TABLE I

Composition of the extracting agent mixtures

| Extraction mixture | Composition [w/w] | |
|---|---|---|
| | toluene | isopropanol |
| A | 100 | 0 |
| B | 30 | 10 |
| C | 20 | 10 |
| D | 50 | 50 |
| E | 10 | 20 |
| F | 10 | 30 |
| G | 0 | 100 |
| | cyclohexane | |
| H | 50 | 50 |

Procedure:

The aqueous solution of methoxyacetic acid was treated at room temperature (about 23° C.) with the extracting agent mixtures mentioned in Table I and stirred at 500 rpm for 30 minutes on a magnetic stirrer. The mixtures were then each transferred to a separating funnel and allowed to stand until phase separation was complete (about 30 minutes). In the batches (E, F, H) in which sodium sulfate had precipitated, the salt was brought into solution again by warming with a hot air blower (to about 30° C.) before phase separation. Three phases were formed in batch H.

An extraction yield of 95% was achieved with batch F. D and E afforded extraction yields of >85% and >90% in each case.

B) Variation of the Extracting Agent/feed Ratio:

Substances Employed:

Aqueous solution of methoxyacetic acid (MEA) having the following composition:

18.5% of methoxyacetic acid (MEA)

about 18% of sodium sulfate

=feed

Various amounts of extracting agent mixture toluene/isopropanol=1:1 (w/w)

=Extraction agent

| Extraction | Feed [g] | Extracting agent [g] | Extracting agent/feed ratio (w/w) |
|---|---|---|---|
| A | 100 | 52.5 | 0.525 |
| B | 50 | 75.0 | 1.5 |
| C | 50 | 100.0 | 2.0 |

| Extraction | Feed [g] | Extracting agent [g] | Extracting agent/feed ratio (w/w) |
|---|---|---|---|
| D | 50 | 125.0 | 2.5 |
| E | 50 | 1500.0 | 3.0 |

Procedure:

The aqueous solution of methoxyacetic acid was treated with the extracting agent mixtures indicated in Table II at room temperature (about 23° C.) and stirred at 500 rpm for 30 minutes on a magnetic stirrer. The mixtures were then each transferred to a separating funnel and allowed to stand until phase separation was complete (about 30 minutes). In the batches in which sodium sulfate had precipitated, the salt was brought into solution again by warming with a hot air blower (to about 30° C.) before phase separation.

Extraction yields of >95% are achieved with a ratio >2.

c) Continuous Extraction:

Substances Employed:

Aqueous solution of methoxyacetic acid (MEA) having the following composition:

17.4% of methoxyacetic acid (MEA)

17.5% of sodium sulfate

Extracting agent toluene/isopropanol 1:1 (w/w)

Figure 1:
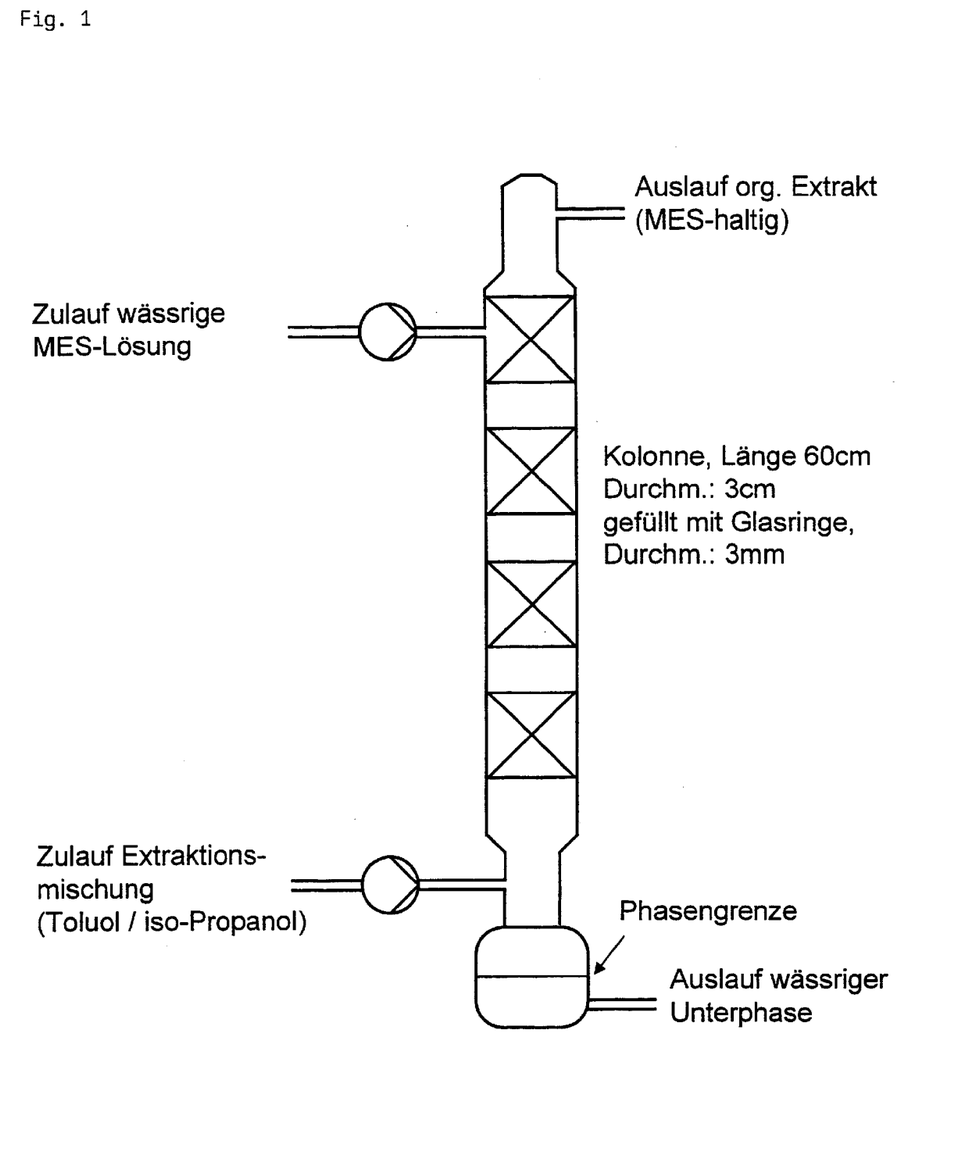
FIG. 1 represents an apparatus for carrying out the extracting step of the inventive process.

Procedure:

The aqueous solution of methoxyacetic acid was diluted with 5% by weight of water at room temperature (about 23° C.) and added at 210 g/h to the head of an extraction column (60 cm long, Ø 3 cm, packed with glass rings Ø 3 mm). 200 g/h of a toluene/isopropanol mixture were fed in countercurrent at the outlet of the extraction column. During the extraction, the column was thermostatted at about 30° C. using a heating tape. The phase boundary was adjusted such that it remained in the middle of the flask attached to the bottom of the column (see FIG. 1). After 8 hours the following were obtained:

| Aqueous lower phase: | 1215 g, density: 1.24 gcm$^{-3}$ |
| Organic extract: | 2062 g, density: 0.87 gcm$^{-3}$ |

The extract (upper phase) contained 12.3% by weight of MEA.

The extraction yield was 91%.

EXAMPLE 3

Esterification of the Acid-containing Extracts as Exemplified by Methoxyacetic Acid

In the extraction of methoxyacetic acid (MEA) with toluene/isopropanol described in Example 2, an extract was obtained which contains even greater amounts of water in addition to the desired valuable product.

As in all H$^+$-catalyzed esterifications of free carboxylic acids with alcohols, the intended esterification of methoxyacetic acid with isopropanol proceeds to an equilibrium.

a) Ion-exchanger Catalysis, in Suspension:

Reaction scheme IV

Esterification in the presence of an ion exchanger

Amounts Employed:

4.4 kg of extract from continuous extraction of an aqueous MEA solution having the following composition:
12.3% of methoxyacetic acid (MEA)
38.1% of isopropanol
38.8% of toluene
10.7% of water
0.1% of Na$_2$SO$_4$ 15 g of acidic ion exchanger Amberlyst W 38

Procedure:

The extract was treated at room temperature with the acidic ion exchanger and heated to reflux with stirring. A ternary heteroazeotrope, consisting of toluene/i-propanol and water (head temperature 76° C.) was distilled off through a 20 cm-long Vigreux column packed with wire packing material at a still temperature of 77 to 79° C. This azeotrope was led through a phase separator and the lower aqueous phase was voided. The upper organic phase was fed back into the column. After 35 hours, lower phase no longer formed in the phase separator. The water content in the still was 2.2% (according to Karl-Fischer titration). According to the $^1$H-NMR spectrum, the methoxyacetic acid had reacted to 85%. The ion exchanger was filtered off, the phase separator was exchanged for a column head and the still contents were fractionally distilled.

Isol. yield of MEIPE: 715.5 g (90% of theory)

Purity of the MEIPE: chem. purity: >99.8% b) Ion-exchanger Catalysis, in a Bypass:

Amounts Employed:

785 g of extract from continuous extraction of an aqueous MEA solution of the following composition:
12.3% of methoxyacetic acid (MEA)
38.1% of isopropanol
38.8% of toluene
10.7% of water
0.1% of Na$_2$SO$_4$ 50 g of acidic ion exchanger Amberlyst W 38

Figure 2:
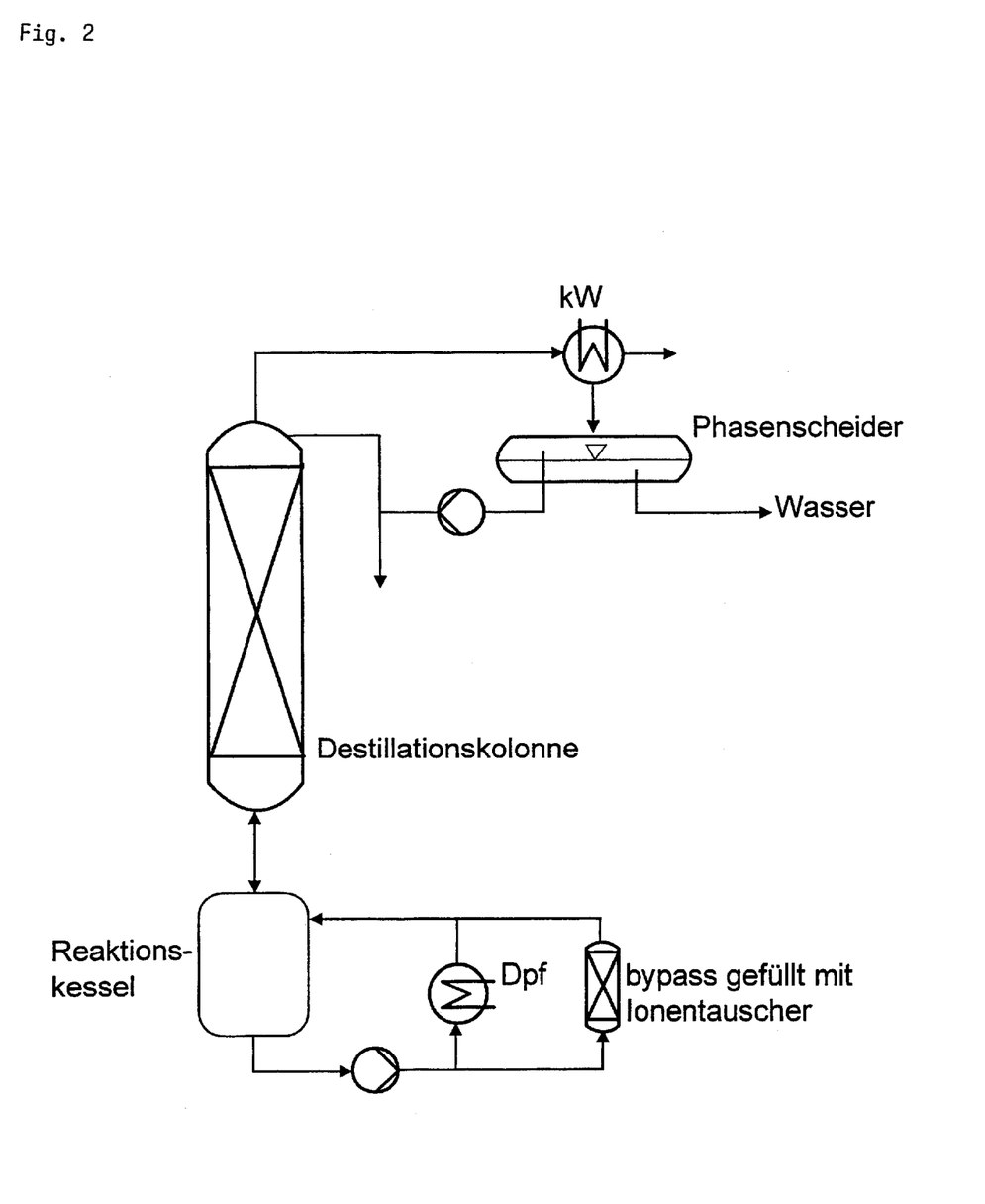
FIG. 2 represents an apparatus for carrying out the esterifying step of the inventive process.

The apparatus can be seen in FIG. 2.

Procedure:

The extract was added at room temperature to a 1 l miniplant vessel. The bottom outlet of the vessel was opened and the mixture was pumped through a column (length 30 cm, Ø: 3 cm) packed with 50 g of acidic ion exchanger Amberlyst W 38 using a membrane pump (capacity: 4.8 l/h). The heating of the miniplant vessel was increased to 140° C. and the resulting distillate was distilled off through a 20 cm-long Vigreux column (packed with wire packing material) at a still temperature of 78 to 80° C. The ternary heteroazeotrope formed, consisting of toluene/i-propanol and water (head temperature 76° C.), was led through a phase separator and the lower aqueous phase was voided. The upper organic phase was fed back into the column. In order to avoid temperature losses, the bypass, which was packed with ion exchanger, was also heated with a heating tape. On emergence from the bypass, the reaction mixture had the same temperature as in the miniplant vessel. After 10 hours, lower phase no longer formed in the phase separator.

The mixture was fractionally distilled.

Isol. yield of MEIPE: 82 g (56% of theory)

The low yield is partly to be attributed to the fact that some of the valuable product remained in the bypass packed with ion exchanger.

Purity of the MEIPE: chem. purity: 98.5% (contains toluene)

c) $H_2SO_4$ Catalysis:

Amounts Employed:

1 kg of extract from continuous extraction of an aqueous MEA solution of the following composition:
10.7% of methoxyacetic acid (MEA)
2.0% of isopropyl methoxyacetate
36.0% of isopropanol
38.0% of toluene
14.0% of water
0.04% of $Na_2SO_4$ Added:

40.0 g of methoxyacetic acid (MEA)
0.8 g of conc. $H_2SO_4$ (0.5 mol %)
100 ml of cyclohexane Procedure:

The extract was mixed with the methoxyacetic acid, sulfuric acid and cyclohexane at room temperature (about 23° C.) and then heated to reflux. A ternary heteroazeotrope, consisting of cyclohexane/i-propanol and water (head temperature 66° C.) was distilled off through a 30 cm-long column packed with wire packing material at a still temperature of 74 to 76° C. This azeotrope was led through a phase separator which had been filled beforehand with cyclohexane and the lower aqueous phase was voided. The upper organic phase was fed back into the column. After 16 hours, the internal temperature had risen to 92° C., the head temperature in the column was 70° C. and the water content in the still was 0.07% (according to Karl-Fischer titration).

According to $^1$H-NMR spectrum, the methoxyacetic acid had reacted to >98%.

The still contents were fractionally distilled.

Isol. (=isolated) yield of MEIPE:

220 g (94% of theory)

Purity of the MEIPE: chem. (=chemical) purity >99,8% d) Azeotropic Esterification of Methoxyacetic Acid/$H_2SO_4$-catalysis:

Reaction scheme VI

Azeotropic esterification under $H_2SO_4$-catalysis:

Amounts Employed:

400 g (4.44 mol) of methoxyacetic acid
400 g of cyclohexane
300 g of toluene
600 g (10 mol) of isopropanol
1 g (0.01 mol) of conc. sulfuric acid (corresponds to 0.2 mol %)

Procedure:

Methoxyacetic acid, cyclohexane, toluene, isopropanol and sulfuric acid were initially introduced at room temperature and then heated to reflux. A ternary heteroazeotrope, consisting of cyclohexane/i-propanol and water (head temperature 66° C.) was distilled off through a 30 cm-long column packed with wire packing material at a still temperature of 74 to 76° C. This azeotrope was led through a phase separator filled beforehand with cyclohexane (contents: about 600 ml). The lower, aqueous phase in this process displaced the corresponding amount of cyclohexane, which flowed back into the reaction mixture via the column. After 6 hours, according to $^1$H-NMR 75% of the methoxyacetic acid had reacted and the water content in the distillation still was 0.58%. After 16 hours water no longer formed in the phase separator; the head temperature in the column had risen to 70° C. and the water content in the still was 0.01% (according to Karl-Fischer titration). According to the $^1$H-NMR spectrum, the methoxyacetic acid had been quantitatively reacted.

The phase separator was exchanged for a column head and the still contents were fractionally distilled.

Isol. yield of MEIPE: 562 g (97% of theory)

Purity of the MEIPE: chem. purity: >99,8%

FIG. 1

Org. extract outlets (MEA-containing)
Aqueous MEA solution outlet
    Column, length 60 cm, diameter: 3 cm
    Packed with glass rings, diameter 3 mm
Extraction mixture outlet
(toluene/isopropanol)
    Phase boundary
    Aqueous lower phase outlet
FIG. 2
    Cooling water
    Phase separator
    Water
Distillation column
Reaction vessel
    Steam
    Bypass, packed with ion exchanger

We claim:

1. A process for the preparation of esters of the general formula I (I)

from compounds of the general formula II contained in aqueous solutions (II), which comprises
  a) extracting the compounds of the general formula II directly or after liberation from their salts in the presence of a $C_1$–$C_8$-alcohol and a water-immiscible solvent and
  b) then esterifying with the $C_1$–$C_8$-alcohol in the presence of a catalyst and of an entraining agent under the conditions of an azeotropic distillation,
where the process steps (a) and (b) can be carried out separately in terms of time and space or else in a successive continuous or batchwise sequence and where the variables and substituents in the formulae I and II have the following meanings:
  $R^1$=F, Cl, —OH, —$OC_1$–$C_{10}$-alkyl,
  $R^2$=H, $C_1$–$C_{10}$-alkyl,
  $R^3$=$C_1$–$C_8$-alkyl,
  Q=—OH, —$O^-K^+$, where $K^+$ is an alkali metal cation or alkaline earth metal cation or an amine,
  n=0, 1 or 2.

2. A process as claimed in claim 1, wherein an acid whose $pK_a$ is lower than that of the compounds of the formula II is used for the liberation of the acid from the salts of the compounds of the formula II.

3. A process as claimed in claim 1, wherein $H_2SO_4$ is used for the liberation of the acid from the salts of the compounds of the formula II.

4. A process as claimed in claim 1, wherein the alcohol used is ethanol, propanol, isopropanol, butanol, hexanol or octanol.

5. A process as claimed in claim 1, wherein the alcohol is simultaneously also used as an organic solvent.

6. A process as claimed in claim 1, wherein process step (a) is carried out at a temperature of from 0° C. to 70° C.

7. A process as claimed in claim 1, wherein the $C_1$–$C_8$-alcohol and the water-immiscible solvent are added separately to the extraction (a).

8. A process as claimed in claim 1, wherein the compounds of the formula II are extracted continuously.

9. A process as claimed in claim 1, wherein the acids of the compounds of the formula II are extracted with a yield of at least 85% in process step (a).

10. A process as claimed in claim 1, wherein the solvents used in process step (a) are apolar organic solvents.

11. A process as claimed in claim 1, wherein the catalyst used for the esterification in process step (b) is an acidic ion exchanger or mineral acids.

12. A process as claimed in claim 1, wherein the entraining agent used in process step (b) is an organic solvent which is immiscible with water and whose boiling point as an azeotrope with the alcohol and the water is lower by at least 85 C than that of the azeotrope of the alcohol and the water.

13. A process as claimed in claim 1, wherein the entraining agent used is cyclohexane.

14. A process as claimed in claim 1, wherein process step (b) is carried out at a pressure of greater than 1 bar.

15. A process as claimed in claim 1, wherein the water content during the esterification in process step (b) is lowered below 0.1%.

16. A process as claimed in claim 1, wherein the yield of the ester of the general formula I in process step (b) is at least 90%.

17. A process as claimed in claim 1, wherein the ester prepared is a $C_1$–$C_8$-alkyl ester of a $C_1$–$C_4$-alkoxyacetic acid.

18. A process for the extraction of compounds of the formula II as claimed in claim 1 from aqueous solutions, which comprises extracting the compounds of the general formula II directly or after liberation from their salts by means of acidification in the presence of a $C_1$–$C_8$-alcohol and a water-immiscible solvent.

* * * * *

UNITED STATES PATENT AND TRADEMARK OFFICE
CERTIFICATE OF CORRECTION

PATENT NO. : 6,720,447 B1
DATED : April 13, 2004
INVENTOR(S) : Ditrich et al.

It is certified that error appears in the above-identified patent and that said Letters Patent is hereby corrected as shown below:

Column 14,
Line 24, "...85 C than..." should read -- ...8º C... --

Signed and Sealed this

Nineteenth Day of April, 2005

JON W. DUDAS
*Director of the United States Patent and Trademark Office*